(12) United States Patent
Cowe

(10) Patent No.: US 10,112,018 B2
(45) Date of Patent: Oct. 30, 2018

(54) INJECTOR APPARATUS

(71) Applicant: OWEN MUMFORD LIMITED, Oxfordshire (GB)

(72) Inventor: Toby Cowe, Oxfordshire (GB)

(73) Assignee: OWEN MUMFORD LIMITED, Oxford (GB)

( * ) Notice: Subject to any disclaimer, the term of this patent is extended or adjusted under 35 U.S.C. 154(b) by 468 days.

(21) Appl. No.: 14/433,157

(22) PCT Filed: Oct. 4, 2013

(86) PCT No.: PCT/GB2013/052590
§ 371 (c)(1),
(2) Date: Apr. 2, 2015

(87) PCT Pub. No.: WO2014/053849
PCT Pub. Date: Apr. 10, 2014

(65) Prior Publication Data
US 2015/0273158 A1      Oct. 1, 2015

Related U.S. Application Data

(60) Provisional application No. 61/709,459, filed on Oct. 4, 2012.

(30) Foreign Application Priority Data

Oct. 4, 2012  (GB) .................................. 1217765.5
May 3, 2013  (GB) .................................. 1308058.5

(51) Int. Cl.
*A61M 5/32*      (2006.01)
*A61M 5/168*     (2006.01)
(Continued)

(52) U.S. Cl.
CPC .......... *A61M 5/329* (2013.01); *A61M 5/1424* (2013.01); *A61M 5/16809* (2013.01);
(Continued)

(58) Field of Classification Search
CPC .. A61M 5/329; A61M 5/3156; A61M 5/3202; A61M 5/31553; A61M 5/344;
(Continued)

(56) References Cited

U.S. PATENT DOCUMENTS 2,705,494 A *  4/1955  Broadwin ......... A61M 5/31555
                                                    422/925
3,759,425 A     9/1973  Lee
(Continued)

FOREIGN PATENT DOCUMENTS

EP    0247824 A2   12/1987
EP    1570873 A1    9/2005
(Continued)

OTHER PUBLICATIONS

International Search Report, dated Jun. 18, 2014, from corresponding PCT application.
(Continued)

*Primary Examiner* — Amber Stiles
(74) *Attorney, Agent, or Firm* — Young & Thompson

(57) ABSTRACT

An injector apparatus is disclosed for use with a container of therapeutic material to deliver a metered dose of therapeutic material therefrom. The apparatus includes a first body portion arranged to be fixed relative to the container and defining a first conduit portion for the delivery of the therapeutic material from the container and a second body slidably connected to the first body and defining a second conduit portion, in fluid communication with the first conduit portion. Relative sliding motion between the first body and second body results in the displacement of one of the
(Continued)

conduit portions into the other conduit portion such that the combined volume of the conduit may be decreased.

16 Claims, 7 Drawing Sheets

(51) Int. Cl.
- *A61M 5/20* (2006.01)
- *A61M 5/24* (2006.01)
- *A61M 5/31* (2006.01)
- *A61M 5/315* (2006.01)
- *A61M 5/34* (2006.01)
- *A61M 5/142* (2006.01)
- *A61M 5/00* (2006.01)

(52) U.S. Cl.
CPC .............. *A61M 5/204* (2013.01); *A61M 5/24* (2013.01); *A61M 5/2429* (2013.01); *A61M 5/3146* (2013.01); *A61M 5/3156* (2013.01); *A61M 5/3159* (2013.01); *A61M 5/31548* (2013.01); *A61M 5/31553* (2013.01); *A61M 5/31593* (2013.01); *A61M 5/3202* (2013.01); *A61M 5/344* (2013.01); *A61M 5/002* (2013.01)

(58) Field of Classification Search
CPC .......... A61M 5/31548; A61M 5/31593; A61M 5/16809; A61M 5/1424; A61M 5/3159; A61M 5/24; A61M 5/2429; A61M 5/3146; A61M 5/204; A61M 5/002

See application file for complete search history.

(56) References Cited

U.S. PATENT DOCUMENTS

| | | | |
|---|---|---|---|
| 4,210,173 A | 7/1980 | Choksi et al. | |
| 5,360,413 A | 11/1994 | Leason et al. | |
| 5,807,346 A * | 9/1998 | Frezza | A61M 5/31553 604/208 |
| 5,988,452 A | 11/1999 | Dent et al. | |
| 6,224,567 B1 | 5/2001 | Roser | |
| 6,364,170 B1 * | 4/2002 | Anderson | B05B 11/0016 222/131 |
| 2004/0007601 A1 * | 1/2004 | Masuda | B65D 47/2075 222/494 |
| 2007/0179439 A1 | 8/2007 | Vogelin et al. | |
| 2011/0108147 A1 | 5/2011 | Carmody et al. | |
| 2011/0282276 A1 | 11/2011 | Abal | |

FOREIGN PATENT DOCUMENTS

| | | |
|---|---|---|
| WO | 9917820 A1 | 4/1999 |
| WO | 0249697 A1 | 6/2002 |
| WO | 2005107847 A1 | 11/2005 |
| WO | 2012059455 A1 | 5/2012 |

OTHER PUBLICATIONS

Great Britain Search Report, dated Apr. 24, 2014, from corresponding GB application.

* cited by examiner

81  Fig. 2E

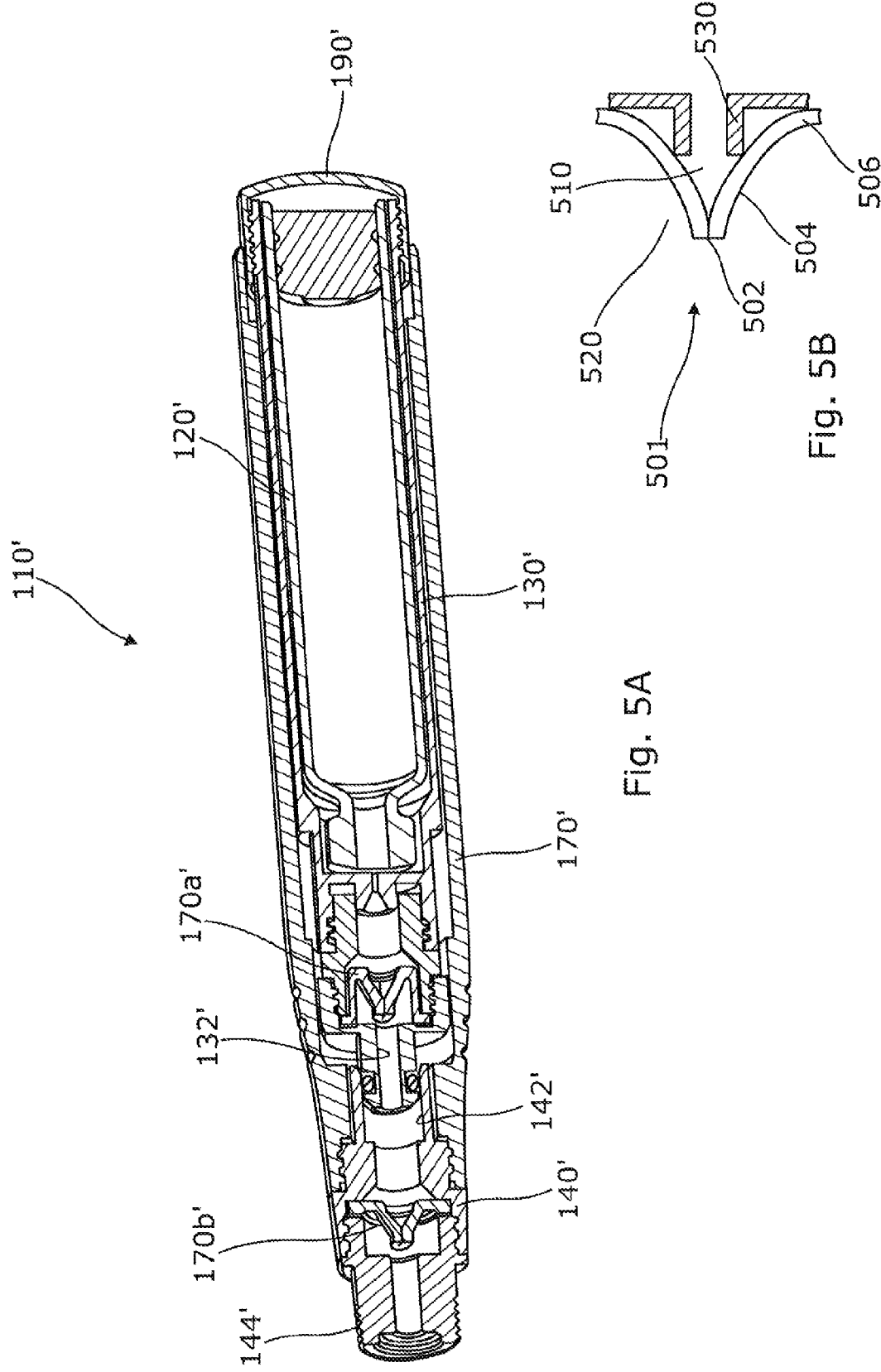

INJECTOR APPARATUS

FIELD OF THE INVENTION

This invention relates to an injector apparatus and in particular, but not exclusively, to such apparatus used for injecting metered doses from a container of therapeutic material, for example of insulin.

BACKGROUND OF THE INVENTION

In a conventional pen injector, such as the Owen Mumford Autopen, container of therapeutic material, for example insulin, is received in a holder which is connected to a pen body. The container may be any suitable container for containing therapeutic material in an injector such as a pen injector. For example, the container may typically be a cartridge or a syringe. In alternate embodiments the cartridge could be integrally formed with or by a portion of the injector (for example the injector body or housing).

A needle is typically removably attached to the pen injector for delivery of the therapeutic material. The pen body is provided with a mechanism arranged to expel successive single metered doses of therapeutic material from the container via the needle. Such mechanisms generally comprise a plunger which is arranged to engage a piston of the cartridge and to move forward by a predetermined increment in response to a user pressing a release button. It will be appreciated that pen injectors are arranged to administer a plurality of repeatable single metered doses and that typically the volume of each individual dose may be variable. Therefore, the mechanism generally further comprises a dosing mechanism, for example a dial, to adjust the movement of the plunger.

It is desirable for pen injectors to be of a compact form so that they can be carried around and used unobtrusively. Further compact injectors may be simple to manufacture, assemble and use with consequent savings in manufacturing and assembly costs, and a lower environmental impact. Accordingly, an alternative injector apparatus has been proposed in the applicants co-pending UK Patent Application GB1217765.5 and U.S. Provisional Patent Application 61/709,459, both having a filing date of 4 Oct. 2012 and from which the present application claims priority (the contents of which is incorporated herein by reference). The alternative injector apparatus disclosed provides an arrangement in which a mechanism is arranged to draw therapeutic material from the cartridge into a conduit by negative pressure and discharge a metered dose from the conduit via said delivery needle. The mechanism may for example be a positive displacement arrangement in which the volume of the conduit (or in communication with the conduit) is varied to discharge the metered dose by positive pressure. Advantageously, the injector assembly does not require a plunger mechanism to expel therapeutic material from the container (rather the negative pressure provided by the mechanism acts to draw the piston forward as the fluid is discharged).

SUMMARY OF THE INVENTION

According to a first aspect of the invention, there is provided an injector apparatus for use with a container of therapeutic material to deliver a metered dose of therapeutic material therefrom, the apparatus comprising:

a first body portion arranged to be fixed relative to the container and defining a first conduit portion for the delivery of the therapeutic material from said container;

a second body slidably connected to the first body and defining a second conduit portion, in fluid communication with the first conduit portion;

wherein relative sliding motion between the first body and second body results in the displacement of one of the conduit portions into the other conduit portion such that the combined volume of the conduit may be decreased.

Thus, embodiments of the invention may provide a relatively simple and convenient means of providing an injector apparatus which utilises a displacement actuation. Advantageously, the part count of the apparatus may be reduced and/or assembly simplified.

A delivery needle is provided at the forward end of the injector apparatus through which the conduit is arranged to deliver therapeutic material. The delivery needle may be provided on the second body. The delivery needle may be a removable needle assembly (for example a single use sterile needle). Accordingly, the forward end of the injector apparatus (for example the forward end of the second body) may be adapted to receive a disposable delivery needle (for example a single use sterile needle). For example the apparatus may be provided with interconnecting features for receiving a snap-fit or screw-fit disposable needle assembly. Alternatively, the needle may be integral with the injector apparatus (in other words, the needle may be permanently attached to the injector apparatus).

The first body portion may be fixed relative to the container by any suitable arrangement. The particular arrangement may, for example, be determined by the overall configuration of the injector apparatus (which may in turn be dependent upon the particular therapeutic material to be delivered).

In some embodiments the injector apparatus may comprise a durable (i.e. reusable) pen injector in which the container of therapeutic material is arranged to be replaceable (and as such the container is not an essential feature of the invention). In such an arrangement, the first body portion may be fixed relative to (or may be integral with) the body of the pen injector such that it is fixed relative to a container when a container is connected to the injector. Alternatively, the first body may be fixed relative to a container holder or carriage which is moveably mounted within the body (and the second body may be fixed relative to the pen body).

In a further embodiment the injector apparatus may comprise a single use injector which may be provided with a container within the pen and is non-removable such that the pen is disposed of after all of the therapeutic material has been expelled therefrom. In such an arrangement, the first body portion may be fixed relative to (or may be integral with) the body of the pen injector and a container may, for example, be irremovably fixed within or integral with the pen injector body. Alternatively the first body may be fixed relative to or formed integrally with the carriage which is moveably mounted within the body (and the second body may be fixed or integral with the pen body).

Alternatively, the apparatus according to an embodiment of the invention could be provided in the form of a multiple or single use attachment which is attached to a container or a housing containing the container. Such an apparatus could, for example, be provided integrally with a needle assembly. For example the apparatus may be arranged to be fitted onto the collar of a container (for example by a screw thread).

The conduit may be substantially aligned with the longitudinal axis of the apparatus (which is generally coincident with the longitudinal axis of both the container and delivery needle). Thus, the second body may typically be axially slidably connected to the first body.

One of the conduit portions may comprise a chamber and the other conduit portion may comprise a piston received within said chamber. The bore of the conduit portion comprising a piston may extend along the axis of the piston. The head of the piston may be formed by an end portion of the wall of the conduit portion. Thus, in use, the combined volume of the conduit comprises the bore of the piston and the chamber volume defined by the other conduit portion and the head of the piston (such that the relative position of the head varies the total volume).

The first and second body may be biased towards an extended position in which the combined volume of the conduit is maximised. For example, a spring may be provided which acts to bias the first and second bodies apart. In some embodiments the apparatus may further comprise a dosing mechanism which may limit the maximised combined volume.

The apparatus may further comprise a catch arranged to hold the first and second body in a retracted position against said bias. The apparatus may further comprise a cap. The cap may be arranged to prevent release of the catch when the cap is in a closed position. Alternatively, the cap may comprise the catch means (for example, the cap may be arranged to engage both the first and second body).

The catch may comprise complimentary interconnecting features on the first and second body. The interconnecting features may be releasably engagable. For example, the complimentary interconnecting features may resiliently engage. Alternatively, in some embodiments (for example a single use injector assembly) the catch may be arranged such that it may be released but is not resettable (for example a frangible or otherwise tamper evident catch may be provided).

The interconnecting features may comprise at least one inwardly projecting tooth member provided on one of the first or second body and arranged to engage a complimentary profiled shoulder (for example a shoulder of a complimentary groove, recess, projection or wall) on the other of the first or second body. One of the tooth member or shoulder may be resiliently deformable to enable disengagement of the interconnecting features. For example, the tooth may be provided on a flexible arm on the front body 40 or rear body 30. The arm may be resiliently deformed so as to allow the tooth member to be disengaged from the shoulder (for example allowing the tooth to deflect over or around the shoulder). The arm may be outwardly deflected from the body during disengagement.

The injector assembly may further comprise a cap which is provided with an internal surface which is shaped and dimensioned so as to prevent the resilient deformation required to enable disengagement of the interconnecting features. For example, the cap may be arranged to prevent movement of the arm when the cap is in a closed position. The internal surface of the cap may be arranged to engage an outer surface of the arm (for example by surrounding and/or abutting the arm). The internal surface may be locally profiled for example by the provision of an inwardly extending protrusion. Thus, the cap may be arranged to prevent outward deflection of the arm when the cap is in a closed position.

The internal surface of the cap may be provided with a shaped profile such that the catch (for example the arm) is unrestrained upon partial removal of the cap. For example, a rearward portion of the cap (which will pass over the catch as the cap is removed in a forward direction from the end of the injector apparatus) may have an increased internal diameter. The internal diameter of the cap may be outwardly stepped or tapered. Alternatively, the internal surface may be shaped by the provision of at least one cut out section. Advantageously, such arrangements may enable the catch to release during the removal of the cap thereby enabling the first and second bodies to be biased apart before the cap is fully removed. This action results in the expansion of the volume of the conduit and may prime the injection device by drawing a therapeutic material from the container into the conduit. Thus, the apparatus may be considered to be self-priming in response to removal of the cap.

The mechanism may further comprise a dose adjuster arranged to enable a user to set the volume of the metered dose. The dose adjuster may be arranged to adjust the displacement of the conduit portions, for example the dose adjuster may set the stroke of the conduit portions. The dose adjuster may comprise a projection on one of the first or second body and at least one cooperating slot on the other of the first or second body, wherein the projection slides along the slot during relative sliding motion of the first and second body and the length of the slot delimits the relative movement (and therefore the actuation stroke of the injector assembly). The dose adjuster may comprise a plurality of slots of different lengths (with the length of each slot corresponding to a predetermined dose). The projection may be selectively brought into engagement with one of said slots to select the required dose. For example, the plurality of slots may be circumferentially distributed around the first or second body and the selective engagement of the projection may be by relative rotational movement of the first and second body.

The injector assembly may include at least one non-return valve. For example a non-return valve may be provided to prevent flow from the conduit to the container. A non-return valve may be provided to prevent flow from the needle to the conduit. The, or each, non-return valve may comprise a flexible membrane extending across an opening and retained on a shoulder surrounding the opening, wherein the flexible membrane further comprises at least one slit positioned proximal to a periphery of the membrane such that the slit overlies the shoulder of the container or injector apparatus.

This arrangement is considered novel and inventive in its own right and, therefore, according to a further aspect of the invention there is provided a non-return valve for a container or injector apparatus for therapeutic material, the non-return valve comprising:

a flexible membrane arranged to extend across an opening and to be retained on a shoulder surrounding said opening; wherein the flexible membrane further comprises at least one slit positioned proximal to a periphery of the membrane such that when the membrane is unreformed the slit overlies the shoulder of the opening of the container or injector apparatus.

According to a further aspect of the invention, there is provided a container for therapeutic material comprising a non-return valve, wherein the non-return valve comprises a flexible membrane arranged to extend across an opening of the container and to be retained on a shoulder surrounding said opening. The flexible membrane may comprise at least one slit positioned proximal to a periphery of the membrane such that the slit overlies the shoulder of the container or injector apparatus. The container may for example be a cartridge.

Typically the flexible membrane is attached to the shoulder at an outermost region. For example, the membrane may be clamped (or otherwise attached, for example bonded) to the shoulder by its peripheral edges. The at least one slit may be inwardly adjacent to the attachment region.

The membrane has a first surface which faces the opening and abuts the shoulder and a second, opposing, surface facing away from the opening.

In a neutral position the slit of the membrane is not aligned with the opening such that the valve may be considered closed. When the membrane is deformed towards the opening (i.e. by being subject to a negative pressure from the first surface or a positive pressure from the second surface) the slit is compressed against the shoulder. In contrast, when the membrane is deformed away from the opening (i.e. by being subject to a positive pressure from the first surface or a negative pressure from the second surface) the membrane is deformed and lifts the slit away from the shoulder of the opening, thus opening the valve. The deformation of the membrane may additionally stretch the slit so as to further open the valve.

The first surface of the membrane may be provided with a profiled surface sized and dimensioned so as to be received within the opening. For example the membrane may be provided with inwardly tapering sides for alignment with the opening. Advantageously, this helps to resist any deformation of the membrane in the non-flow direction (i.e. towards the opening). For example the profiled surface may comprise a plug (which may for example be arranged to be seated within the opening when the valve is in the closed position). Thus, when the membrane is deformed towards the opening the profiled surface of the membrane will be urged towards its seated position in the opening and may form a pinch seal around the edge of the opening (and inboard of the at least one slit).

The flexible membrane may comprise a plurality of slits at spaced apart locations about the periphery of the membrane, each slit being positioned to overlie the shoulder. The, or each, slit may comprise an actuate slit.

A biasing means may be arranged to urge the flexible membrane towards a closed position. Thus, it will be appreciated that the biasing means may reinforce the seal of the non-return valve.

Whilst the invention has been described above it is to be understood that it includes any inventive combination of the features set out above or in the following description or drawings.

BRIEF DESCRIPTION OF THE DRAWINGS

Specific embodiments of the invention will now be described in detail, by way of example only, and with reference to the accompanying drawings in which:

FIGS. 2A to 2F are schematic three-dimensional cross sectional views showing the sequence of operation of the first embodiment;

FIG. 5A is a schematic cross sectional view of a pen injector according to a fourth embodiment of the invention; and FIG. 5B is a schematic cross sectional view of the duckbill valve according to one or more embodiments of the invention.

DETAILED DESCRIPTION OF EMBODIMENTS

Front as used herein will be understood to refer to the end of the injector assembly (or components thereof) which, in use, are closest to the delivery needle delivery end of the injector (i.e. the end which is pointed at the skin). Rear as used herein will be understood to refer to the end of the injector assembly (or components thereof) which, in use, are furthest from the delivery needle delivery end of the injector (i.e. the end which is pointed away from the skin). Forward and rearward will, likewise, be understood to refer to the directions orientated towards the front and rear of the injector assembly.

Figure 1A:
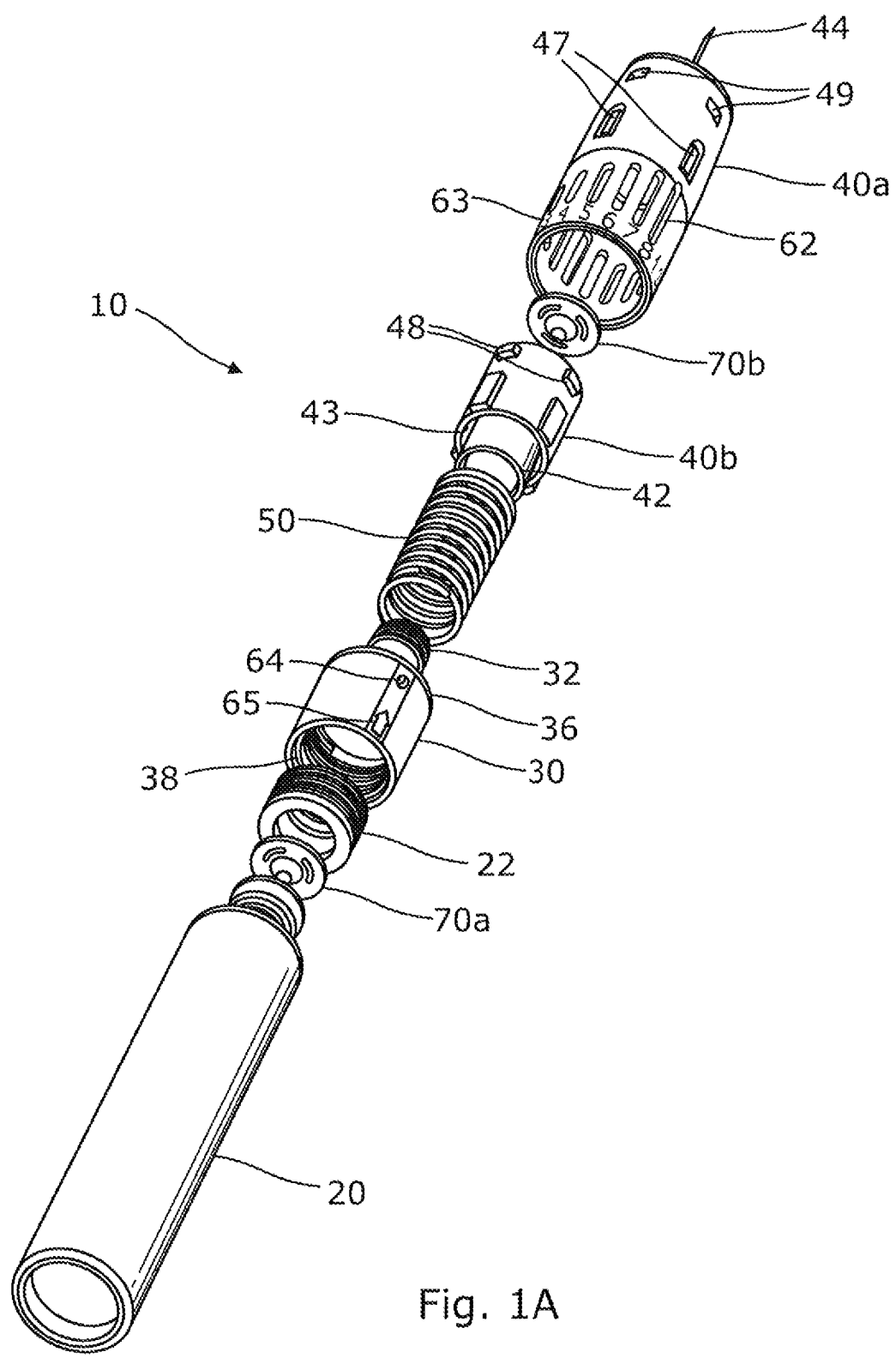
FIG. 1A is an exploded schematic three dimensional view of an injector according to a first embodiment of the invention.
Figure 1B:
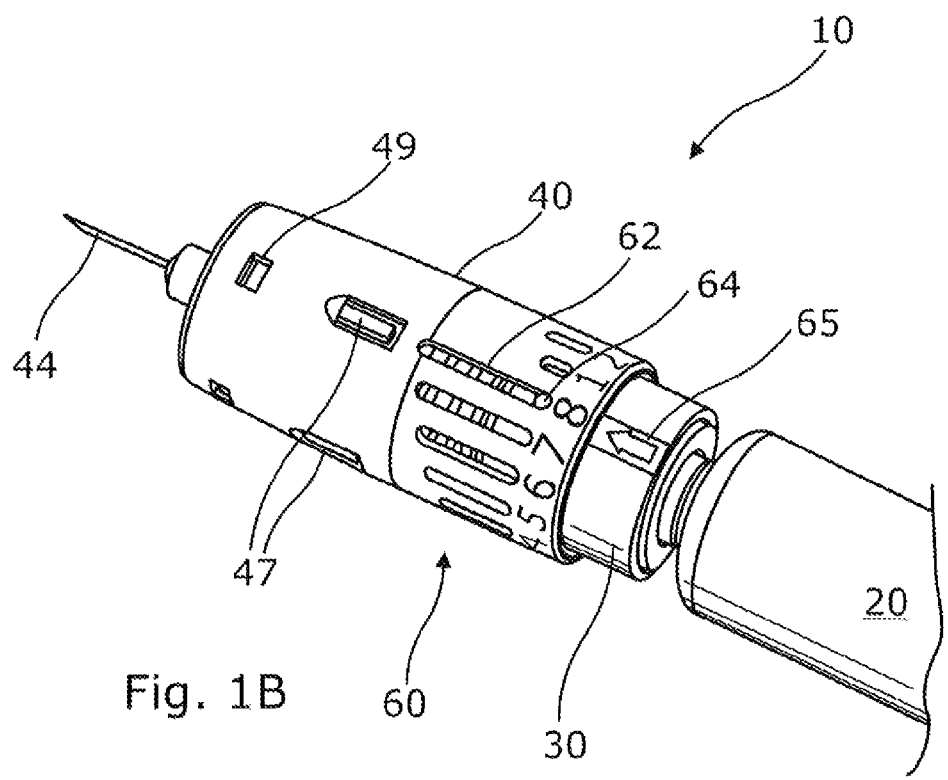
FIG. 1B is an assembled schematic three dimensional view of an injector according to the first embodiment of the invention.
Figure 1C:
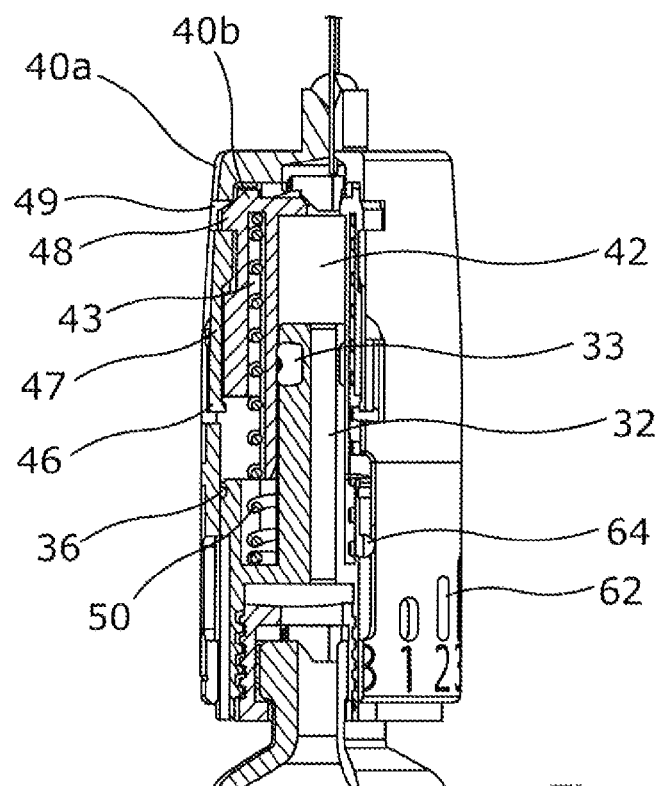
FIG. 1C is a schematic three dimensional partial cross sectional view of an injector according to the first embodiment of the invention.

An injector apparatus 10 in accordance with a first embodiment of the invention is shown in FIG. 1 (with an exploded view in FIG. 1A, an assembled view in FIG. 1B and a partial cross section in FIG. 1C). The injector apparatus is adapted for use with a container of a therapeutic material such as insulin. In the illustrated embodiment, the container is a cartridge 20. In this embodiment the injector apparatus 10 is arranged to be provided as an integral attachment which is attached to the forward end of a cartridge 20. The injector apparatus 10 extends from a threaded rearward opening 38 for attachment to a threaded collar 22 provided on the cartridge 20 to a needle 44 at its forward end. In the illustrated embodiment the needle 44 is formed integrally with the injector apparatus 10 (such that the injector apparatus may be considered a single-use device) but a conventional removable needle may alternatively be provided.

The injector apparatus 10 comprises a first rear body 30 which includes a threaded connection such that the rear body 30 may be fixed to the cartridge 20. A second front body 40 is connected at the front of the first body 30 and arranged to be axially slidable relative to the fixed first body 30. A portion of the front body 40 extends rearwardly over and around the rear body 30. A compression spring 50 is provided between the rear body 30 and movable body 40 so as to bias the front body 40 towards an extended position.

Complimentary interconnecting features (the function of which will be described in detail below) are provided on the rear body 30 and front body 40. The interconnecting feature on the rear body 30 comprises an outwardly facing groove 36. The interconnecting features on the front body 40 comprises a plurality of resilient, axially extending arms 47 each carrying a inwardly projecting tooth 46 sized and dimensioned to be received within said groove.

An axially extending conduit is defined through the rear body 30 and front body 40 for the discharge of the therapeutic material from the cartridge 20 via the needle 44. The conduit is defined by a first conduit portion 32 in the rear body 30 and a second conduit portion 42 in the front body 40. The conduit portions are coaxially aligned and the first conduit portion 32 is sized and positioned such that it is received within the second conduit portion 42. As best seen in FIG. 1C, the second conduit portion 42 provides a cylindrical chamber and the first conduit portion 32 forms a piston received within the chamber. It will be noted that the thickness of the walls of the first conduit portion 32 are selected such that the outer diameter closely conforms to the inner diameter of the chamber formed by the second conduit portion 42. A seal 33 is provided near the forward end of the first conduit portion 32 for sealingly engaging the sides of the first conduit portion 42.

The front body 40 is formed from two separate body components 40a and 40b. The exterior component 40a includes the needle 44 (or needle retention features) at its front and part of a dosing mechanism 60, in the form of dosing slots 62 (which will be described in detail below) at its rear. The interior component 40b defines the conduit portion 42 and is provided with an annular slot 43 for receiving and retaining the spring 50. The components 40a, 40b are provided with a snap fit arrangement by means of a plurality of lugs 48 on the interior moulding 40b which are received and retained in corresponding cut-outs 49 of the exterior component 40a.

During assembly of the front body 40 a non-return valve 70b (which is described in detail below) is positioned between the components 40a, 40b such that it is clamped across the forward end of the conduit 42. The non-return valve 70b is, thus, arranged to prevent reverse flow from the needle 44 to the conduit 42. A further non-return valve 70a (of substantially identical construction to the non-return valve 70b) is provided at the rear of the conduit 32 to prevent reverse flow from the conduit 32 to the cartridge 20. The non-return valve 70a is clamped to the cartridge 20 by the threaded collar 22 (although it will be appreciated that alternatively the valve 70a could be provided on the rear body 30 at the rear of the conduit 32).

The general principle of the operation of the injector assembly 10 utilises the axial sliding motion of the front body 40 to provide a telescopic action between the conduit portions 32 and 42. In any given axial position of the front body 40 the total combined volume of the conduit 32/42 is the volume of the first conduit portion 32 plus the volume of the chamber in the second conduit portion 42 which is forward of the end of the first conduit portion 32 (in other words, the volume is proportional to the spacing between the front of the first 32 and second 42 conduit portions). Thus, if the front body 40 is moved forward the total effective volume is increased and if the front body 40 is moved rearward the total effective volume is decreased. Any increase in volume of the conduit 32/42 creates a negative pressure which acts to open non-return valve 70a whilst drawing non-return valve 70b back onto its valve seat. As such therapeutic material will be drawn from the cartridge 20 into the conduit 32/42. Any decrease in volume of the conduit 32/42 creates a positive pressure which acts to open non-return valve 70b whilst compressing non-return valve 70a back onto its valve seat. As such therapeutic material will be discharged from the conduit 32/42 via the needle 44. A dosing mechanism 60 is provided for setting the range of motion of the injector apparatus 10 in use (and will be described in further detail below).

The operation of the injector apparatus will now be described in detail with reference to FIG. 2A to 2F showing the sequential steps of operation.

Prior to use, the injector apparatus 10 may be provided in a sealed unit within a cap 80. The rear of the cap is provided with a sterile sealing member 82 bonded to a flange 84 at the rear of the cap. Within the cap 80, the injector apparatus is in a "closed" configuration with the front body 40 in its rearmost position with respect to the rear body 30 and the spring 50 compressed. Each inwardly projecting tooth 46 is seated within the corresponding groove 36 so as to retain the closed configuration against the bias of the spring 50. It will be noted that the inner surface of the cap 80 closely conforms to the outer profile of the injector apparatus 10 in the closed configuration and the cap 80 is in its closed position. In particular, the portion of the cap 80 adjacent to the interconnecting features is arranged such that it abuts or closely conforms to the exterior surface of the arms 47. The cap may, for example, include local inwardly projecting protrusions 81 (as best seen in FIG. 2E) to ensure that the interior surface abuts the arms 47. As such, when the cap 80 is in the closed position the arms 47 are restrained from the outward resilient deflection required for the tooth 46 to disengage the grove 36.

Figure 2A:
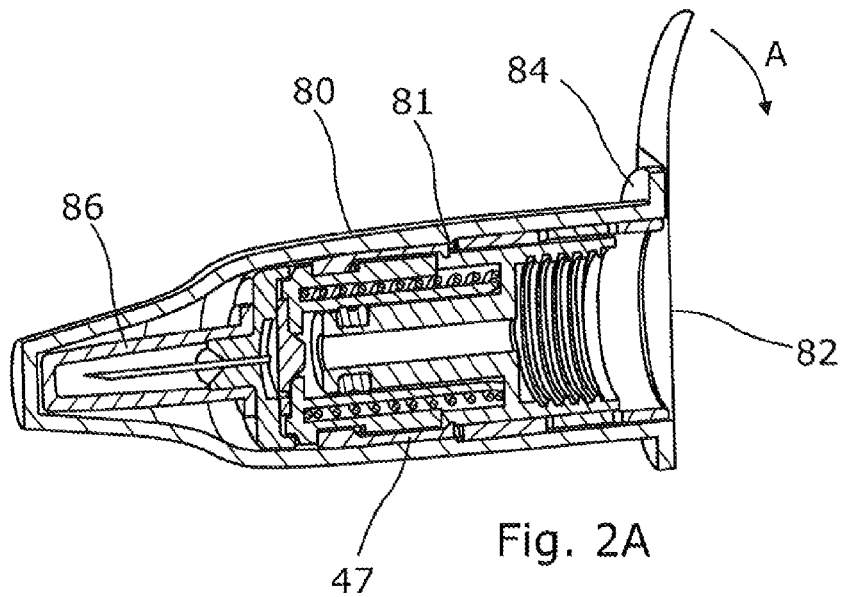
Figure 2B:
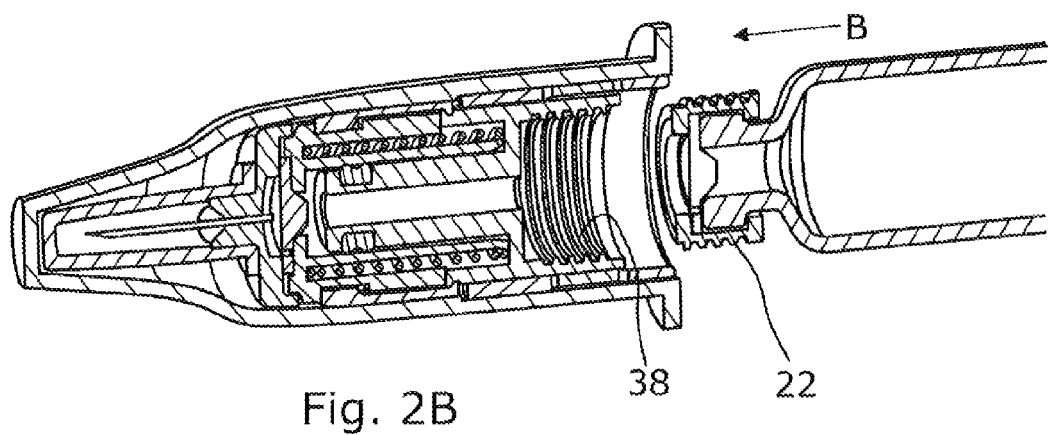
Figure 2C:
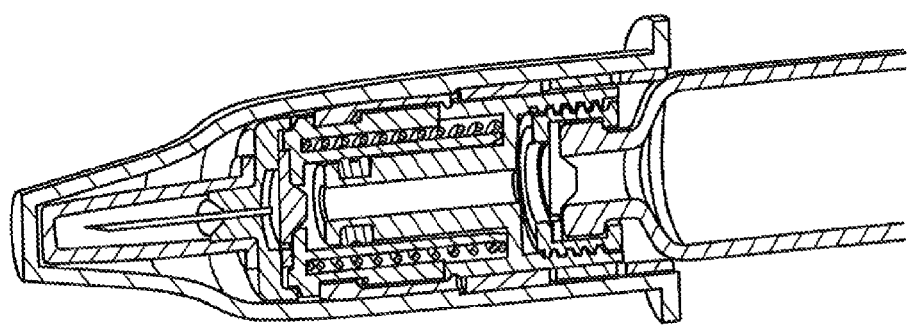

In order to prepare the injector apparatus 10 for use the user must first remove the sealing member 82 by tearing the tab portion in the direction of arrow A as shown in FIG. 2A. Once removed the threaded connection 38 at the rear of the rear body 30 is exposed and may be connected to a cartridge 20 having a suitably threaded collar 22, as shown in FIGS. 2B and 2C.

Figure 2D:
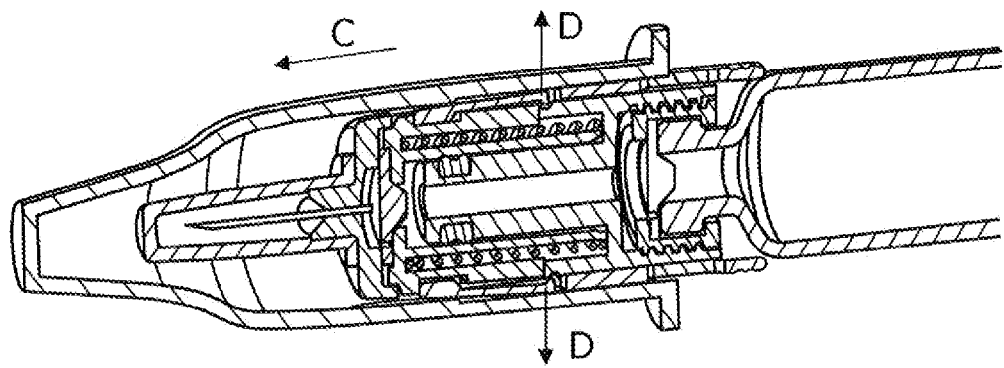

Next the user removes the cap 80 in a forward direction as shown by arrow C (in FIGS. 2D and 2E). In doing so the protrusions 81 are moved out of alignment with the arms 47 such that the arms become aligned with a reward portion of the cap 80 which has a greater internal diameter than the undeflected diameter of the front body 40 at the location of the arms. Thus, the biasing force of the spring 50 may act to urge the front body 40 and rear body 30 apart such that the interconnecting teeth 46 are urged out of the groove 36 deflecting the arm 44 carrying the teeth 46 outwardly into the space between the cap 80 and the injection apparatus 10. Once the interconnecting features disengage the front body 40 slides axially forward (within the cap 80) in the direction of arrow E under the driving force of the spring 50. The forward movement of the front body 40 expands the volume of the conduit 32/42 and acts to draw therapeutic material from the cartridge 20 into the injection apparatus 10. Thus, the injector apparatus may, advantageously, self-prime when the user removes the cap 80 (although it will be appreciated that in some arrangements further manual priming action, i.e. by actuating the injector apparatus, may be required to ensure that the conduit 32/42 is fully charged with therapeutic material before use).

Figure 2F:
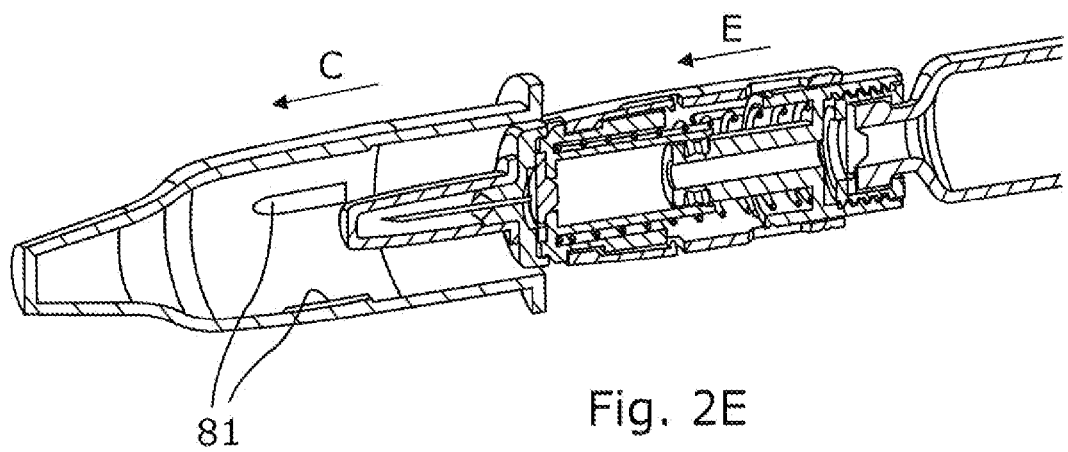
Figure 2F:
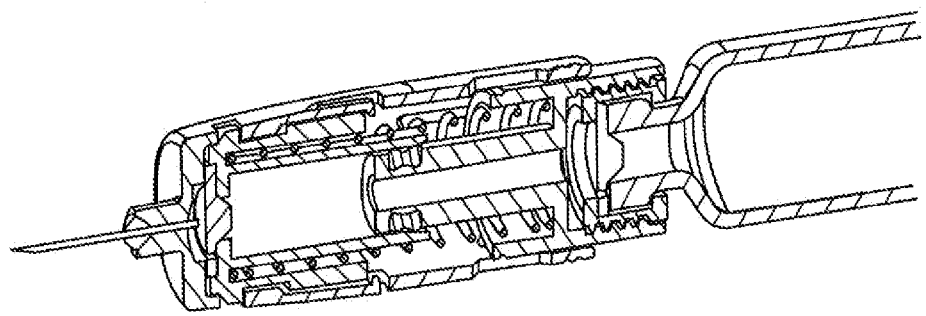

Finally after the cap 80 has been fully removed the needle sheath 86 is removed from the needle 44 such that the apparatus is ready for use as shown in FIG. 2F. In order to use the injector apparatus 10 the user simply compresses the body sections 30 and 40 together so as to discharge a metered dose from the needle 44 by compression of the conduit 32/42 (unless a dose adjustment is first required as will be described below). Depending upon the type of therapeutic agent to be delivered this may be performed by compressing the cartridge 20 against the skin surface (i.e. in a "jabbing" action as is common with emergency medication injectors such as those for Epinephrine) or in a more controlled manner by restraining the front body 40 in position against the skin while advancing the rear body 30.

Prior to delivery, the dosing mechanism 60 (as best seen in FIG. 1) may be used to select a required dose. The dosing mechanism comprises an outwardly projecting dosing projection 64 (or alternatively, a plurality of projections) provided on the rear body 30 which is arranged to be received within one of a plurality of axially aligned dosing slots 62 in an overlying portion of the movable body 40. The projection 64 and slots 62 are relatively rotatable such that the projection 64 may be aligned with any one of the slots 62 in use (and will typically be arranged to "click" or "snap fit" into a chosen slot to provide an audible and tactile indication of the dose selection). A dose indicator 65 may be provided on the body 30 adjacent to the projection 64 to provide a visual indicator of the selected dose (in conjunction with a scale making 63 associated with the slots 62). During axial sliding motion between the bodies 30, 40 of the injector apparatus (during actuation and/or priming), the projection 64 travels along the slot 62 into which it has been aligned and the ends of the slot 62 provides physical stops which delimit the relative motion of the bodies 30, 40. The length of each slot 62 is chosen to provide a predetermined range of motion which corresponds to a particular change in volume of the conduit 32/42 and therefore a desired dose being discharged via the needle 44.

Figure 3A:
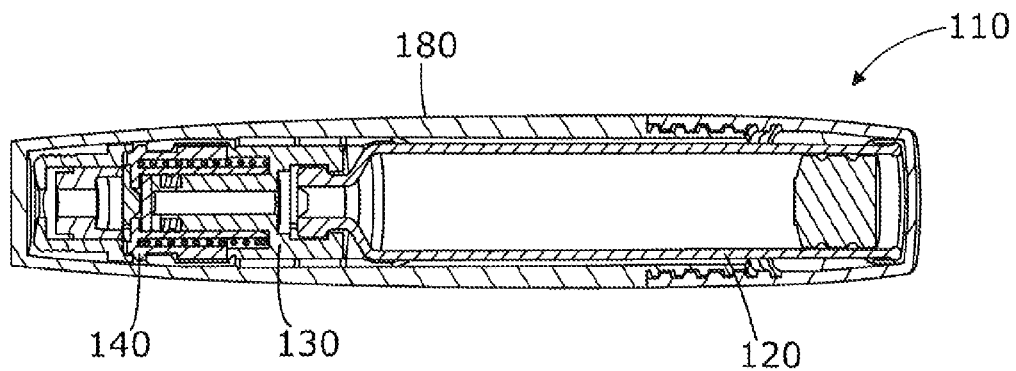
FIG. 3A is a schematic three dimensional cross sectional view of an injector according to a second embodiment of the invention.
Figure 3B:
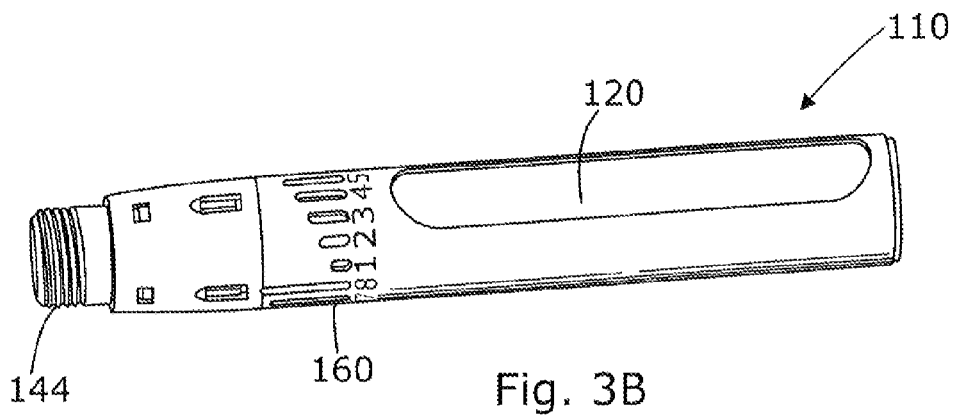
FIG. 3B is a schematic three dimensional view of the injector according to the second embodiment of the invention (with the cap removed)
Figure 3C:
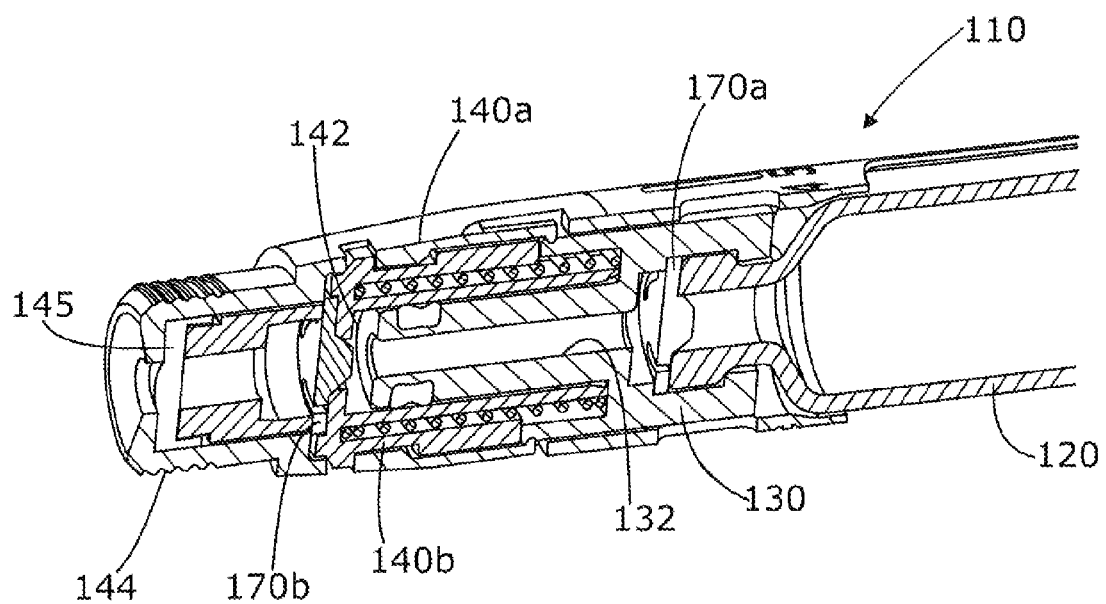
FIG. 3C is a detailed schematic three dimensional partial cross sectional view of an injector according to the second embodiment of the invention.

FIG. 3 shows an alternate embodiment in which the injection apparatus 110 is provided in the form of a more conventional pen injector having a body which encloses the cartridge 120. The skilled person will appreciate that the actuation of the injector apparatus 110 is substantially identical to that of the injector apparatus of the first embodiment 10. The cartridge 120 may be replaceable by an end user such that the injector apparatus 110 is reusable or as illustrated may be substantially irremovably mounted within the injector apparatus 10 such that the injector apparatus is intended to be disposable (e.g. once the therapeutic material has been fully used). It will be noted that in the disposable embodiment illustrated the rear body 130 is clamped directly to the neck of the cartridge 120 (with the valve 170a held therebetween) this removes the need for a threaded collar on the cartridge 120.

The body surrounding the cartridge may be formed integrally with the outer component 140a of the front body 140 such that the cartridge 120 and rear body 130 (which are fixed relative to one another but slidably connected to the front body 140) will, in use, axially slide within the outer body.

The cap 180 may comprise a two-part casing which substantially encloses the injector apparatus 110 as shown in FIG. 3A.

In contrast to the earlier embodiment, this embodiment is provided with a threaded needle attachment 144 rather than an integral needle 44 such that a disposable, single-use, needle may be attached to the injector apparatus 110. It may be noted that a septum 145 may be provided behind the needle attachment 144 (and forward of the non-return valve 170b) which will be pierced in use by a needle assembly mounted to the needle attachment 144.

The non-return valve 70, 170 used in embodiments of the invention will now be described in further detail. As best seen in FIG. 1A the valve 70 comprises a flexible membrane, typically in the form of a generally circular disc. The membrane is provided with a plurality (and in the illustrated example three) of actuate slits 72 which are positioned at an outer region of the flexible member and are generally circumferentially aligned. The slits 72 are through-slits but in some arrangements it may be desirable to initially provide a partial depth slit which will rupture into a through slit upon first use (e.g. when pressurised above a desired pressure)—for example so as to initially seal the valve. A central region of the flexible membrane has a profiled surface including an increased thickness convex bulge 74 on one side. The bulge 74 is in use positioned to face the opening upon which the valve is to be used and is sized and dimensioned to provide a plug within said opening (as will be explained below). The bulge 74 has tapered sides to assist with alignment of with the opening. The opposing surface of the membrane to the bulge 74 may also be profiled. For example the surface may have an at least partially concave profile as shown by the dashed profile 75 in FIG. 4b. The concave profile may be arranged such that the Bulge is hollowed. This profile enables pressure opposing that shown in the direction P to act to reinforce the seal such that the bulge 74 acts on the inside diameter of the chamber as well as upon the front face.

Figure 4A:
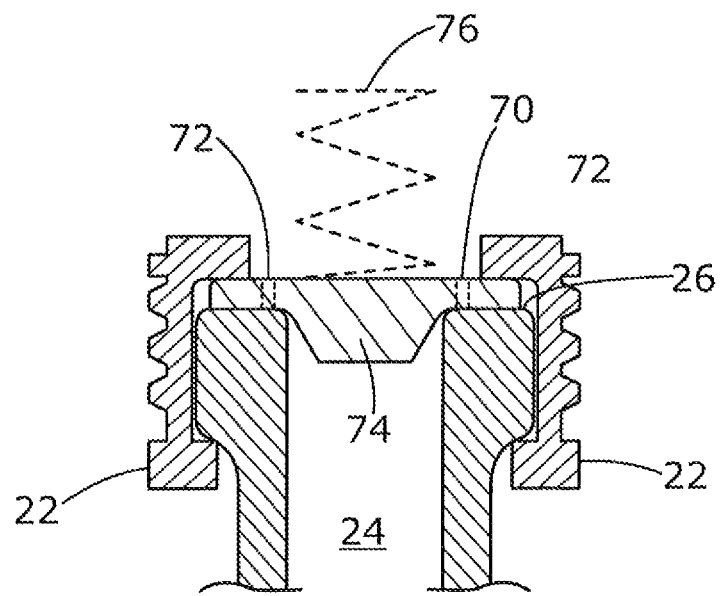
FIGS. 4A and 4B are schematic cross sectional views of a non-return valve for use with embodiments of the invention.
Figure 4B:
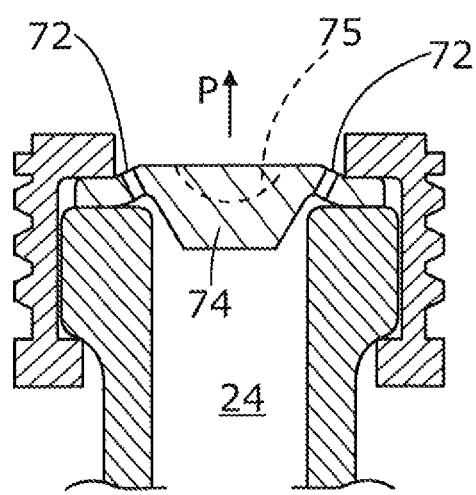

The operation of the non-return valve will be described with reference to FIGS. 4A and 4B. As shown in FIG. 4A the membrane of the valve 70 is provided across an opening 24 (for example the opening of the cartridge 20). The membrane is attached to a shoulder 26 of the opening 24 by its peripheral edges (for example the membrane is clamped to the edge by a collar 22). The actuate slits 72 are positioned adjacent to the peripheral edge at an outward region of the membrane such that they overly the shoulder 26. The bulge 74 extends into the opening 24 and an edge of the bulge may engage the corner between the shoulder 26 and opening 24.

In its natural state (FIG. 4A) the opening is sealed by the bulge 74 and the slits 72 do not allow the flow of fluid as they are seated on the shoulder 26. The valve 70 allows flow in the direction of arrow P by deflection of the membrane (as shown in FIG. 4B). When subjected to net pressure in the flow direction (shown by arrow P), the central region of the membrane is deflected upwards (as shown in the figure) lifting the bulge 74 from engagement with the sides of the opening 24. The slits 72 are also lifted from their seat (and may additionally be resiliently deformed so as to increase their opening) enabling the flow of fluid from the opening 26. When subjected to net pressure in the reverse flow direction, the membrane is compressed towards the shoulder 26. This compression both urges the bulge 74 against the sides of the opening and the slits 72 against their seat on the shoulder such that the opening is sealed and resists reverse flow of fluid.

Optionally, a spring means 76 (shown in dashed lines in FIG. 4A) may be provided which acts to urge the non-return valve 70 towards its closed position and helps to reinforce the seal of the valve. In such an arrangement, the net pressure must overcome the force of the spring 76 in order to open the valve.

FIG. 5a shows a further pen injector 110' in accordance with an embodiment of the invention which generally operates by the same displacement principle as the first and second embodiments. The pen injector comprises a housing 170' which receives a cartridge or syringe 120' of a similar type to that shown in the preceding embodiments. The cartridge 120' is provided within a carriage formed as part of the rear body 130'. The rear body 130' and the cartridge are thus fixed relative to one another but relatively slidably moveable relative to the forward body 140'. An actuation button 190' is provided at the rearward end of the rear body 130' and may be removable attached (e.g. by a screw thread) such that the cartridge may be replaceable in use. The forward end of the injector 110' is adapted to receive a delivery needle and may, therefore, include an external thread 144'. A conduit 132'/142' extends in a generally axial direction from a rearward end in communication with the cartridge 120' to the forward end proximal to the delivery needle. As in the preceding embodiments a first non-return valve 170*a*' is provided at the rear of the conduit 132'/142' and a second non-return valve 170*b*' is provided at the front of the conduit 132'/142'.

As in the previous embodiments, the conduit portions are coaxially aligned. The first conduit portion 132' is sized and positioned such that it is slidably received within the second conduit portion 142'. A seal is provided on the outer wall of the second conduit portion 132' to sealingly engage the inner wall of the first conduit portion 142'.

In use, the injector 110' is actuated by a user urging the actuation button 190 at the rear of the housing 170' forwardly which moves the cartridge 120' (and the rear body 130'/carriage in which it is mounted) forward relative to the housing 170'. The forward body 140' is fixed relative to the housing 170' such that the forward movement of the rear body 130' displaces the first conduit portion 132' (which is fixed relative to the cartridge 120') forward into the second conduit 142' (which is fixed relative to the housing 170). Thus, the volume of the conduit is reduced and, as a result of the direction of the one-way valves 170*a*' and 170*b*' a metered dose is expelled from the conduit 442. As in the preceding embodiments the mechanism rearward 130' and forward 140' bodies may be biased towards an expanded position such that the first conduit portion 132' moves rearwardly relative to the second conduit portion 142' when the release button 190' is released to draw a new dose into the conduit 142'/132'.

It may be noted that the particular form of the non-return valves 170*a*' and 170*b*' differ from those of the first and second embodiments (although it will be appreciated that the valves of any of the illustrated embodiment may be considered interchangeable). The valves 170*a*' and 170*b*' are so called "duckbill" valves. The duckbill valve 501 is shown in isolated cross section in FIG. 5*b* and has an axially extending portion 506 having a generally conical (or similar) cross sectional profile which extends from a flange 504 (which may additionally include an attachment section at its periphery as shown in FIG. 4*a*). The axially extending section 506 includes a split or opening 502 which is urged open when pressured from an interior side 510 of the axial portion but is urged closed when pressurised from an exterior side 520. In order to increase the accuracy of the duckbill valve (and therefore the dose accuracy) the duckbill valve may be positioned over an axial extending boss 530 formed within the conduit (as shown in FIG. 5*b*). This arrangement has been found to be particularly advantageous in preventing the side portions of the axially extending region 506 of the duckbill valve 501 from collapsing or bulging inwardly during opening and closing of the valve 501.

Although the invention has been described above with reference to one or more preferred embodiments, it will be appreciated that various changes or modifications may be made without departing from the scope of the invention as defined in the appended claims.

The invention claimed is:

1. An injector apparatus for use with a container of therapeutic material to deliver a metered dose of therapeutic material therefrom, the apparatus comprising:
   a first body configured to be fixed relative to the container and defining a first conduit portion for the delivery of the therapeutic material from said container;
   a second body slidably connected to the first body and defining a second conduit portion, in fluid communication with the first conduit portion, the second body being provided with or configured to receive a delivery needle at a forward end of the injector apparatus through which the therapeutic material is delivered in use from the container via a conduit defined by the first conduit portion and the second conduit portion, the first body and the second body being biased towards an extended position in which the volume of the conduit is maximized;
   a first non-return valve configured to prevent flow from the conduit to the container;
   a second non-return valve configured to prevent flow from the needle to the conduit; and
   a catch configured to hold the first body and the second body in a retracted position against said bias,
   wherein relative sliding motion between the first body and the second body results in the displacement of one of the conduit portions into the other conduit portion such that the volume of the conduit may be decreased.

2. The injector apparatus as claimed in claim 1, wherein one of the conduit portions comprises a chamber and the other conduit portion comprises:
   a piston received within said chamber, and
   a bore extending along the axis of the piston.

3. The injector apparatus as claimed in claim 1, further comprising a cap configured to prevent release of the catch in a closed position.

4. The injector apparatus as claimed in claim 1, wherein said catch comprises complimentary interconnecting features on the first body and the second body.

5. The injector assembly as claimed in claim 1, wherein the first non-return valve comprises a flexible membrane extending across the conduit and retained on a shoulder, the flexible membrane comprising at least one slit positioned proximal to a periphery of the membrane such that the slit overlies the shoulder of the container or injector apparatus.

6. The injector assembly as claimed in claim 5, wherein the membrane has a first surface which faces an opening, the first surface being provided with a profiled surface sized and dimensioned to be received within the opening.

7. The injector assembly as claimed in claim 5, wherein the slit comprises an actuate slit.

8. The injector assembly as claimed in claim 5, wherein the flexible membrane comprises a plurality of slits at spaced apart locations about the periphery of the membrane, each slit being positioned to overlie the shoulder.

9. The injector assembly as claimed in claim 5, further comprising a biasing system configured to urge the flexible membrane towards a closed position.

10. An injector apparatus for use with a container of therapeutic material to deliver a metered dose of therapeutic material therefrom, the apparatus comprising:
   a first body arranged to be fixed relative to the container and defining a first conduit portion for the delivery of the therapeutic material from said container;
   a second body slidably connected to the first body and defining a second conduit portion, in fluid communication with the first conduit portion, the first conduit portion and the second conduit portion defining a conduit, the first body and the second body being biased towards an extended position in which the volume of the conduit is maximized; and
   a catch configured to hold the first and second body in a retracted position against said bias, the catch comprising complimentary interconnecting features on the first body and the second body,
   wherein the interconnecting features comprise at least one inwardly projecting tooth member provided on a flexible arm on one of the first or second body and configured to engage a complimentary profiled shoulder on the other of the first or second body, and wherein the arm is capable of being resiliently deformed to allow the tooth member to be disengaged, wherein relative sliding motion between the first body and second body results in the displacement of one of the conduit portions into the other conduit portion such that the volume of the conduit may be decreased.

11. The injector assembly as claimed in claim 10, further comprising a cap configured to prevent release of the catch in a closed position, the cap being provided with an internal surface which is shaped and dimensioned to prevent movement of the arm when the cap is in a closed position.

12. The injector assembly as claimed in claim 11, wherein the internal surface of the cap is configured to engage an outer surface of the arm and prevent outward deflection of the arm when the cap is in a closed position.

13. The injector assembly as claimed in claim 11, wherein the internal surface of the cap is provided with a shaped profile such that the arm is unrestrained upon partial removal of the cap.

14. An injector apparatus for use with a container of therapeutic material to deliver a metered dose of therapeutic material therefrom, the apparatus comprising:
 a first body configured to be fixed relative to the container and defining a first conduit portion for the delivery of the therapeutic material from said container;
 a second body slidably connected to the first body and defining a second conduit portion, in fluid communication with the first conduit portion, the second body being provided with or configured to receive a delivery needle at a forward end of the injector apparatus through which the therapeutic material is delivered in use from the container via a conduit defined by the first conduit portion and the second conduit portion;
 a first non-return valve configured to prevent flow from the conduit to the container;
 a second non-return valve configured to prevent flow from the needle to the conduit;
 a dosing mechanism comprising a projection on one of the first body or the second body and at least one cooperating slot on the other of the first body or the second body,
 wherein the projection slides along the slot during relative sliding motion of the first and second body, and the length of the slot delimits the actuation stroke of the injector assembly, and
 wherein relative sliding motion between the first body and the second body results in the displacement of one of the conduit portions into the other conduit portion such that the volume of the conduit may be decreased.

15. The injector assembly as claimed in claim 14, wherein the at least one cooperating slot comprises a plurality of slots of different lengths, and
 wherein the projection is configured to be selectively brought into engagement with one of said slots to select the required dose.

16. The injector assembly as claimed in claim 15, wherein the slots are circumferentially distributed around the first or second body, and the selective engagement of the projection is by relative rotational movement of the first body and the second body.

* * * * *